United States Patent [19]

Hochberg

[11] Patent Number: 5,188,803
[45] Date of Patent: Feb. 23, 1993

[54] DEVICE FOR PREPARING A MEDICAL SENSOR FOR USE

[75] Inventor: Howard M. Hochberg, Woodinville, Wash.

[73] Assignee: Abbott Laboratories, Abbott Park, Ill.

[21] Appl. No.: 278,610

[22] Filed: Dec. 1, 1988

[51] Int. Cl.$^5$ ............................................. B01L 11/00
[52] U.S. Cl. ....................................... 422/99; 422/100; 422/101; 422/102; 435/291; 435/296
[58] Field of Search ................. 436/18, 8, 19; 422/99, 422/91, 90, 112, 102, 101, 68, 61, 100; 204/415, 403, 401; 128/303.18; 435/296, 291

[56] References Cited

U.S. PATENT DOCUMENTS

| | | | |
|---|---|---|---|
| 3,654,926 | 4/1972 | Rietman | 604/416 |
| 3,682,162 | 8/1972 | Colyer | 128/303.18 |
| 3,842,836 | 10/1974 | Ogle | 604/416 |
| 3,865,548 | 2/1975 | Padawer | 422/68 |
| 4,515,752 | 5/1985 | Miramanda | 422/99 |
| 4,689,308 | 8/1987 | Gerhard | 436/18 |

FOREIGN PATENT DOCUMENTS 716477  2/1932  France ............................... 604/415

Primary Examiner—Robert J. Warden
Assistant Examiner—Timothy M. McMahon
Attorney, Agent, or Firm—Christensen, O'Connor, Johnson & Kindness

[57] ABSTRACT

The apparatus includes a container (26) having an open upper end into which is fitted a stopper (20). From the lower peripheral surface of the stopper (20) depends a membrane (24) which forms a chamber containing one calibrating fluid (28). The stopper (20) is adapted to permit a medical probe to extend therethrough, the hub (16) needle (14) and sensor (12) of which extend beneath the membrane (24). Another calibrating fluid (30) is located in the container (26) beneath the membrane (24). The membrane (24) is capable of maintaining a fluid-tight seal as it is punctured by the needle (14) and of re-sealing itself when the needle (14) is removed, without permitting contamination of the one calibrating fluid (28) by the other calibrating fluid (30) and vice versa.

13 Claims, 1 Drawing Sheet

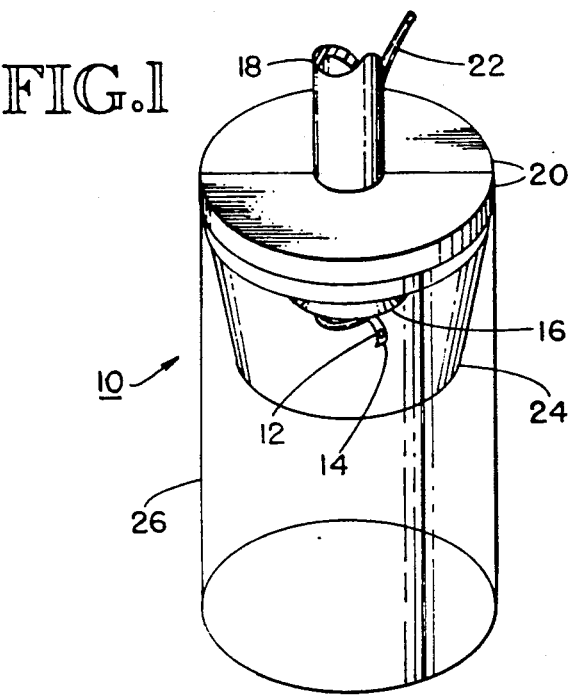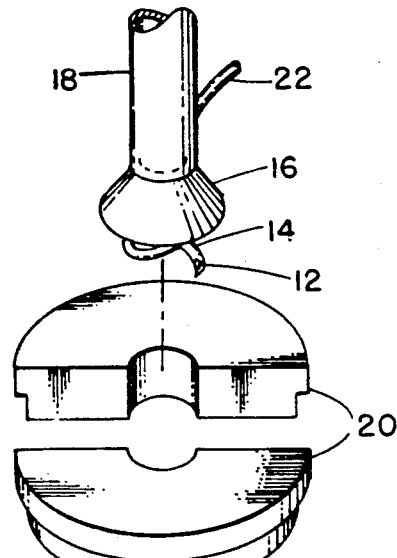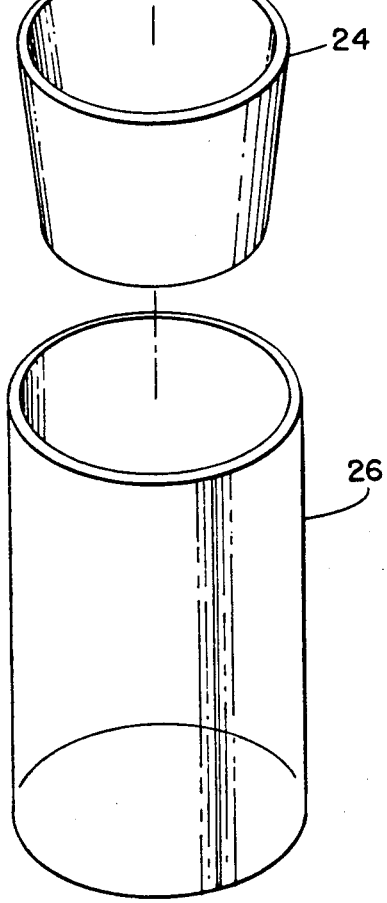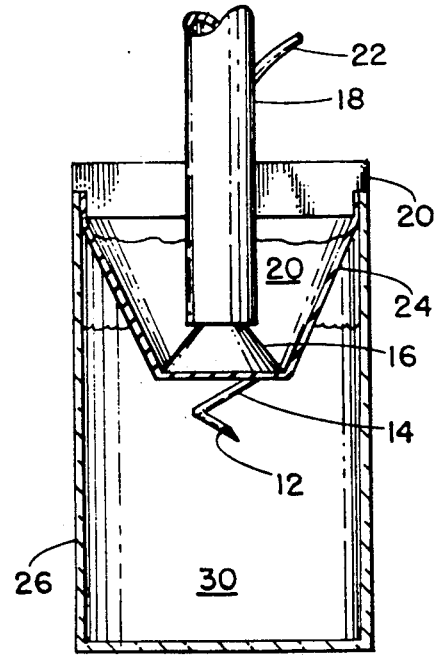

DEVICE FOR PREPARING A MEDICAL SENSOR FOR USE

TECHNICAL FIELD

This invention relates to the storage and preparation for use of a medical sensor for use. More particularly the present invention relates to the calibration of a medical sensor in at least two distinct calibrating fluids of different values while maintaining the sterility of the sensor before, during and after calibration is completed.

BACKGROUND ART

Calibration of medical sensors a short time before their use is desirable to help ensure that the sensor yields accurate results. Many sensors are unstable due to the materials comprising the sensors of or their design.

As an example the output signals from state-of-the-art sensors may vary due to simple changes in environment, such as temperature changes, while other sensors are subject to change simply from aging. Further, many sensors do not have a linear response over their stated range. For these sensors, calibration must be performed over a relatively small range to insure accuracy. Another example concerns the calibration of chemical sensors, such as a pH sensor, used for fetal monitoring. With such sensors, it is necessary that calibration be accomplished by measuring at least two operating or sensing points, because the operating response of such sensors is not always linear.

The calibration of medical sensors has typically been accomplished by using two separate containers, each containing a different calibration fluid, with each calibration fluid being at or near the opposite ends of the expected range to be measured. A trained technician would first record the sensor's output with the sensor submerged in the first calibrating fluid. Then the technician would move the sensor from the first container to the second container, where a second calibrating fluid would be used to produce a second calibrating point. Since the two calibrating fluids are at opposite ends of the expected range to be measured, the sensor would be accurate over that range after being calibrated. For example, if calibrating a pH sensor for use where an expected value of a pH measurement is 7.20±0.20, one calibrating fluid would have a pH of 7.0 and the other calibrating fluid would have a pH of 7.40.

When using the two container method of calibration as discussed above, the problem of maintaining sterility of the sensor and the calibrating fluids during calibration and thereafter of the sensor prior to actual use thereof becomes critical. When moving the sensor from one container to the other sensor one of the calibrating fluids may easily be contaminated.

Sterility is a major concern in the use of medical sensors since any contamination of the needle and sensor may lead to further complications, caused by infection. Further, if either the sensor or the calibrating fluids become contaminated, the accuracy of the sensor or of the calibration procedure may be substantially reduced, rendering the results misleading, which may cause a doctor to make a wrong prognosis or treatment decision.

In using the two container method mentioned above, there is substantial risk that contamination will occur due to exposure of the sensor to air sensor and the calibrating fluids. In order to alleviate this problem a solution was disclosed in U.S. Pat. No. 4,689,308 to Gerhard. Gerhard discloses a method of calibrating a sensor wherein the sensor is isolated in a double container. The sensor is first calibrated in a first calibrating fluid and then the vessel containing the first calibrating fluid is released from its seal, causing the first calibrating fluid to mix with a second calibrating fluid contained within the second, outer vessel, creating the fluid in which a second calibration is made. While Gerhard is a significant improvement over previous sensor calibration procedures, the present invention further simplifies multiple point calibration, by using two separate calibrating fluids without mixing thereof, which alleviates the problem of having to measure exact amounts of each calibrating fluid to be placed in the double container and maximizes the time the sensor remains in a sterile environment.

Another requirement of any good calibration system is that the sensor must be kept hydrated at all times. The present invention not only provides a system wherein the sensor remains hydrated, but also maintains the sterility of the sensor during subsequent storage until the time of actual use of the sensor.

SUMMARY OF THE INVENTION

The present invention includes a container which is open at one end and which defines a first chamber capable of holding a first calibrating fluid and a stopper means which is adapted to fit in said open end of said container, said stopper means having an opening which extends therethrough. A probe includes a needle portion which extends beneath the stopper when the probe is operatively positioned therein, the needle portion including a medical sensor. The probe can be moved rotatably and perpendicularly in relation to the stopper while a fluid-tight seal between the stopper and the probe is maintained. The invention also includes means within said container which defines a second chamber, positioned so that it is about said needle portion of the probe and the medical sensor. The second chamber is capable of holding a second calibrating fluid. The defining means is punctured by a needle portion of the probe and is self-sealing around said needle and capable of resealing itself after the needle is withdrawn. The invention further includes means for removing the probe from the stopper.

BRIEF DESCRIPTION OF THE DRAWINGS

FIG. 1 is an environmental view of the present invention showing the sensor to be calibrated in a first calibration position.

FIG. 2 is a cross-sectional view of the article of FIG. 1, showing the sensor to be calibrated in a second calibrating position.

FIG. 3 is an exploded view of the article of FIG. 1.

BEST MODE FOR CARRYING OUT THE INVENTION

Generally, the present invention is a device for preparing a medical sensor for use, comprising two calibrating fluids segregated by a non-permeable membrane which can be punctured by a needle attached to the sensor, without damaging the integrity or sealability of the membrane with the device also adapted to prevent contamination of the sensor and calibrating fluids.

For purposes of illustration, the invention is described in the context of a particular medical sensor, i.e. a pH sensor, and a particular application featuring calibration of the sensor at two operating points by the use of calibrating fluids that have two different pH values.

It should be understood that the principles of the present invention are not limited to pH sensors or calibration per se at two operating points, nor is the invention limited to necessarily only applications of medical sensors but could conceivably be used in other calibration applications.

It should be further understood that the invention could be used to calibrate a sensor at more than two sensing points by modifying the initial calibration fluid in one chamber after calibration has occurred with that initial calibration fluid and the sensor moved to the other chamber containing the other calibration fluid. The calibration fluids could be liquids or gases depending on the characteristics of the membrane used to segregate them.

FIG. 1 shows the device of the present invention, generally at 10. A pH sensor 12 is placed at or near the end of a spiral shaped needle 14 that is attached to a hub 16, which in turn is attached to the applicator tool rod 18 The above described elements are collectively referred to as a probe. The probe is held in place by a splittable stopper 20, which is made of a resilient material. The stopper 20 may be split in halves, quarters or fragmented into a reasonable number of sections in order to allow the probe hub 16 to be conveniently positioned beneath the stopper with tool rod 18 extending upwardly through the central opening in stopper 20. The opening in the center of stopper 20 is sized so as to create an interference fit with the tool rod 18. The stopper 20 firmly holds and seals the tool rod 18 in place due to the resilient characteristics of stopper 20, with hub 16, needle 14 and sensor 12 beneath the underside of stopper 20 and the tool rod 18 and. communication wire 22 extending through and on the opposite side of stopper 20.

Attached to stopper 20 is a membrane 24 that is prophylactic in defining a first chamber in which are located probe hub 16, needle 14, and sensor 12. The membrane 24 is made of latex, or similar elastomeric material, such that when punctured by the needle 14 it will seal around the needle and then when the needle is withdrawn from the membrane, the membrane will reseal itself, without allowing any fluid movement from one side to the other. This is similar in operation to a drug bottle cover where a syringe is pushed through the cover to withdraw the drug through the cover and then the syringe is removed.

The combination of sensor 12, needle 14, hub 16, stopper 20, and membrane 24 is then placed into a cylindrical container 26 of small diameter and height, with the top of the container 26 sized to receive the outside diameter of the stopper 20 thereby holding the pieces of the stopper 20 together. In the preferred embodiment, a cylindrical container 26 will be made of a clear or transparent material for reasons that will be made clear later.

Referring now to FIG. 2, during the assembly of the device, the chamber formed by the membrane 24 and the bottom surface of stopper 20 is substantially filled by a first calibrating fluid. Therefore, the probe hub 16 along with needle 14 and sensor 12 are submerged in the first calibrating fluid. A second calibrating fluid 30 is placed in the container 26 such that when the stopper 20, along with membrane 24, is placed into the container 26, the second calibrating fluid will substantially fill the container 26, thereby coming into contact with the convex-shaped exterior surface of a membrane 24.

In this particular application, it is important that sensor 12 be continually hydrated due to the characteristics of the pH sensor being used; however, it would be possible to arrange the fluid levels such that the sensor 12 would not be continually submerged in the first calibrating fluid 28.

A short time before the probe is to be used, sensor 12 must be calibrated. The first calibration point is measured with the sensor 12 submerged in the first calibrating fluid 28 which is contained within the first chamber formed by the membrane 24 and the stopper 20, with said calibrating fluid 28 being either toward the high end or the low end of the pH range expected to be measured when actually using the sensor. When calibration has been completed in the first calibrating fluid 28, the applicator tool rod 18 is rotated and pushed downwardly until contact is made with membrane 24. Further downward motion results in the needle 14 puncturing the membrane 24, such that the sensor 12 is now in the second calibrating fluid 30. The resilient nature of the stopper 20 allows the tool rod 18 to move while a seal is still maintained between the two elements. The applicator tool rod 18 is pushed down through stopper 20 until the probe hub 16 contacts the membrane 24 thereby improving the seal made between the membrane 24 and the needle 14. Since the container is clear, it is easy for the technician to see when the probe hub has made contact with the membrane.

Once the needle 14 and probe 12 are submerged in the second calibrating fluid 30, a second calibration is performed, the second calibrating fluid being at the opposite end of the pH range expected to be measured from the first calibrating fluid 28, i.e. if the predicted pH is to be 7.2, the first calibrating fluid 28 may have a pH of 7.4, whereas the second calibrating fluid 30 would have a pH of 7.00. Also, according to a preferred embodiment, the container 26 is made of a clear or transparent material such that a color change in either the first calibrating fluid 28 or the second calibrating fluid 30 can easily be seen by the technician. The first calibrating fluid 28 or the second calibrating fluid 30 are formulated such that if a leak should occur in the membrane 24, the calibrating fluid being contaminated changes color. Therefore, if the integrity of membrane 24 is compromised, the technician will be able to see a color change and use a different method of calibration or dispose of the entire device.

The force required on the applicator tool rod in order for the needle 14 to puncture the membrane 24 is essentially the same force that is required when placing the needle 14 into the scalp of a fetus (not shown). This is a great advantage in that it allows the physician the opportunity to get the "feel" for the force required to implant the probe before actually implanting it in a fetus.

An advantage of the present invention over the prior art is that since the two calibrating fluids are not mixed, an exact measurement of the volume of each calibrating fluid placed in the container 26 or within the chamber between membrane 24 and the stopper 20 is not important. In the prior art method, the volume of each fluid would have to be very accurate achieve the desired pH level when the two fluids are mixed together. If it is desirable to have more than two calibration points, one of the calibrating fluids can be modified while the needle 14 and sensor 12 are submerged in the other calibrating fluid. This can be accomplished, for instance, by gas diffusion through a tube placed in either the stopper 20 or the container 26 or by another method with multiple calibrating points, the other calibrating fluid is modified once the needle 14 and sensor 12 are drawn back into the calibrating fluid that was just modified Hence, multiple (more than 2) calibration points are possible.

The needle 12 is moved back into the first calibrating fluid 28 in a procedure reversing that used for moving it through the membrane 24, i.e. the applicator tool rod 18 is rotated and withdrawn upwardly with a motion reversing that used to puncture the membrane 24. As the tool rod 18 is rotated and pulled upwardly the needle 14 moves back through the membrane 24 into the first calibrating fluid 28, such that when the needle 14 moves to the position where it is no longer contacting the membrane, 24, the membrane 24 reseals itself, thereby maintaining the integrity of separation between the first calibrating fluid 28 and the second calibrating fluid 30. The number of times that the needle 14 may puncture membrane 24 is dependent on the After the medical sensor (probe) has been calibrated and it is ready to be used, the stopper 20, with the membrane 24 still attached thereto, along with the probe, are all removed simultaneously from the container 26. Since the probe is still in the first calibrating fluid 28 which is contained in the chamber formed between membrane 24 and stopper 20, the sterility of needle 14 is maintained while preparation for its implantation is completed. When the probe is finally needed by the clinician, the stopper 20 can be conveniently broken apart into two or more pieces, away from the tool rod 18, freeing the probe for use.

Although the preferred embodiment has been described for purposes of illustration, it should be understood that various changes and modifications may be incorporated in such embodiment, as discussed above, without departing from the spirit of the invention, as defined by the claims which follow.

I claim:

1. A device for storing and calibrating a medical sensor while preventing contamination thereof, said medical sensor including a needle portion, comprising:
   a container open at one end, said container including a first chamber capable of holding a first calibrating fluid;
   a stopper sized to fit in said open end of said container, said stopper having an opening therethrough to receive the medical sensor, and sized so that the medical sensor can be moved rotatably and perpendicularly in relation to said stopper while a fluid-tight seal between said stopper and said medical sensor is maintained; and
   an elastomeric material formed into a wall that defines a second chamber within said container, proximate said stopper and said open end of the container, said second chamber being capable of holding a second calibrating fluid, said wall separating the first and second calibrating fluids and being flexible and puncturable by the needle portion of the medical sensor, for self-sealing around said needle portion and resealing after said needle portion is withdrawn.

2. The device of claim 1, wherein the stopper is removable from the container.

3. The device of claim 1, wherein said elastomeric material comprises an elastomeric membrane.

4. The device of claim 3, wherein said elastomeric membrane is attached to said stopper, said second chamber depending below said stopper.

5. The device of claim 1, wherein said container is made of a substantially transparent material so that a color change in one of the first and second calibrating fluids is apparent.

6. The device of claim 5, wherein a color change occurs in a resulting fluid if one of said first and second calibrating fluids mixes with the other.

7. The device of claim 1, wherein said stopper and said second chamber are removable from the container as an integral unit.

8. The device of claim 1, wherein said separating means is characterized in that a predefined force is necessary to penetrate it with said needle portion.

9. The device of claim 1, including means for introducing a substance into the container to change a calibration characteristic of one of said first and second calibrating fluids.

10. The device of claim 1, wherein said stopper is made of resilient material.

11. The device of claim 9, wherein said means for introducing the substance into the container to change the calibration characteristic of one of said first and second calibrating fluids includes a tube that extends through the stopper.

12. The device of claim 9, wherein said means for introducing the substance into the container to change the calibration characteristic of one of said first and second calibrating fluids includes a tube that extends through the wall of the container.

13. A device for storing and calibrating a medical sensor while preventing contamination thereof, comprising:
   a container having an open end, said container being divided into a first chamber capable of receiving a first calibrating fluid and a second chamber capable of receiving a second calibrating fluid, said second chamber being removable from the container through the open end;
   a stopper sized to fit said open end of the container and including an opening in which the medical sensor can be retained when stored within the second chamber; and
   an elastomeric membrane sealingly separating said first chamber from said second chamber, said elastomeric membrane being characterized by its ability to seal around the medical sensor when perforated thereby, as the medical sensor is advanced from the second around the medical sensor when perforated thereby, as the medical sensor is advanced from the second chamber into the first chamber, and its ability to reseal when the medical sensor is withdrawn from the first chamber, thereby preventing mixing of the first and second calibrating fluids.

* * * * *

UNITED STATES PATENT AND TRADEMARK OFFICE
CERTIFICATE OF CORRECTION

PATENT NO. : 5,188,803
DATED : February 23, 1993
INVENTOR(S) : H.M. Hochberg

It is certified that error appears in the above-indentified patent and that said Letters Patent is hereby corrected as shown below:

Col. 1, line 17, after "sensors" delete "of"
Col. 1, line 26, "sensor," should read --sensor--
Col. 1, line 53, "sensor" should read --sensor,--
Col. 1, line 66, after "air" delete "sensor"
Col. 3, lines 21 & 22, "rod 18" should read --rod 18,--
Col. 3, line 35, "and." should read --and--
Col. 3, line 54, "stopper 20" should read --stopper 20,--
Col. 3, line 68, "a" should read --the--
Col. 4, lines 7 & 8, after "used," insert --the-- and continue with the same paragraph
Col. 4, line 62, after "accurate" insert --to--
Col. 5, line 1, after "method" insert --of changing the pH of a calibrating fluid. To continue--
Col. 5, line 4, "modified" should read --modified.--
Col. 5, line 19, after "the" insert --calibrating fluids and the membrane 24 material used--
Col. 6, lines 55-57, after "second" delete "around the mdical sensor when perforated thereby, as the medical sensor is advanced from the second"

Signed and Sealed this

Eighteenth Day of January, 1994

Attest:

BRUCE LEHMAN

Attesting Officer   Commissioner of Patents and Trademarks